United States Patent
McGuckin, Jr. et al.

(10) Patent No.: US 9,439,650 B2
(45) Date of Patent: *Sep. 13, 2016

(54) APPARATUS AND METHOD FOR RESECTIONING GASTRO-ESOPHAGEAL TISSUE

(71) Applicant: REX MEDICAL, L.P., Radnor, PA (US)

(72) Inventors: James F. McGuckin, Jr., Radnor, PA (US); Peter W. J. Hinchliffe, Downington, PA (US)

(73) Assignee: REX Medical, L.P., Radnor, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/018,000

(22) Filed: Feb. 8, 2016

(65) Prior Publication Data

US 2016/0151065 A1    Jun. 2, 2016

Related U.S. Application Data

(63) Continuation of application No. 13/856,819, filed on Apr. 4, 2013, now Pat. No. 9,271,727, which is a continuation of application No. 11/471,126, filed on Jun. 20, 2006, now Pat. No. 8,424,741, which is a continuation of application No. 10/855,908, filed on May 27, 2004, now Pat. No. 7,090,684, which is a continuation of application No. 10/062,760, filed on Jan. 31, 2002, now Pat. No. 6,835,199.

(60) Provisional application No. 60/265,469, filed on Jan. 31, 2001.

(51) Int. Cl.
*A61B 17/068*   (2006.01)
*A61B 17/10*    (2006.01)
*A61B 17/072*   (2006.01)
*A61B 17/3205*  (2006.01)
*A61B 1/273*    (2006.01)
(Continued)

(52) U.S. Cl.
CPC ........... *A61B 17/105* (2013.01); *A61B 17/068* (2013.01); *A61B 17/072* (2013.01); *A61B 17/07207* (2013.01); *A61B 17/3205* (2013.01); *A61B 1/2736* (2013.01); *A61B 17/00234* (2013.01); *A61B 2017/00278* (2013.01); *A61B 2017/00827* (2013.01); *A61B 2017/07214* (2013.01); *A61B 2017/07221* (2013.01); *A61B 2017/2905* (2013.01); *A61B 2017/2923* (2013.01)

(58) Field of Classification Search
CPC .................................................. A61B 17/1152
USPC ........................... 227/179.1, 180.1; 606/139
See application file for complete search history.

(56) References Cited

U.S. PATENT DOCUMENTS 4,473,077 A    9/1984  Noiles
4,485,817 A   12/1984  Swigget
(Continued)

*Primary Examiner* — Nathaniel Chukwurah

(57) ABSTRACT

A system for stapling tissue comprises a flexible endoscope and an operative head including a pair of opposed, curved tissue clamping jaws sized to pass through an esophagus, the jaws being moveable with respect to one another between an open tissue receiving configuration and a closed tissue clamping configuration, a first one of the curved jaws including a stapling mechanism and a second one of the jaws including a staple forming anvil surface, the stapling mechanism including staple slots through which staples are fired arranged in a row extending from a proximal end of the first jaw to a distal end thereof in combination with a control handle which, when the operative head is in an operative position within one of a patient's stomach and esophagus, remains outside the patient, the control handle including a first actuator for moving the jaws relative to one another and a second actuator for operating the stapling mechanism.

30 Claims, 11 Drawing Sheets

(51) Int. Cl.
  *A61B 17/00* (2006.01)
  *A61B 17/29* (2006.01)

(56) References Cited

U.S. PATENT DOCUMENTS

| | | | |
|---|---|---|---|
| 4,488,523 A | 12/1984 | Shichman |
| 4,505,414 A | 3/1985 | Filipi |
| 4,610,383 A | 9/1986 | Rothfuss et al. |
| 4,671,445 A | 6/1987 | Barker et al. |
| 5,040,715 A | 8/1991 | Green et al. |
| 5,100,419 A | 3/1992 | Ehlers |
| 5,139,513 A | 8/1992 | Segato |
| 5,190,203 A | 3/1993 | Rodak |
| 5,197,649 A | 3/1993 | Bessler et al. |
| 5,258,008 A | 11/1993 | Wilk |
| 5,271,543 A | 12/1993 | Grant et al. |
| 5,326,013 A | 7/1994 | Green et al. |
| 5,330,486 A | 7/1994 | Wilk |
| 5,355,897 A | 10/1994 | Pietrafitta et al. |
| 5,389,098 A * | 2/1995 | Tsuruta | A61B 17/00234 606/142 |
| 5,392,978 A | 2/1995 | Velez et al. |
| 5,395,030 A * | 3/1995 | Kuramoto | A61B 1/00087 227/179.1 |
| 5,403,326 A | 4/1995 | Harrison et al. |
| 5,411,508 A | 5/1995 | Bessler et al. |
| 5,425,738 A | 6/1995 | Gustafson |
| 5,433,721 A | 7/1995 | Hooven et al. |
| 5,441,507 A | 8/1995 | Wilk |
| 5,507,426 A * | 4/1996 | Young | A61B 17/07207 227/176.1 |
| 5,562,694 A | 10/1996 | Sauer et al. |
| 5,571,116 A | 11/1996 | Bolanos et al. |
| 5,582,611 A | 12/1996 | Tsuruta et al. |
| 5,582,615 A | 12/1996 | Foshee et al. |
| 5,645,209 A * | 7/1997 | Green | A61B 17/07207 227/175.2 |
| 5,657,921 A | 8/1997 | Young et al. |
| 5,662,260 A | 9/1997 | Yoon |
| 5,667,517 A | 9/1997 | Hooven |
| 5,868,760 A | 2/1999 | McGuckin, Jr. |
| 5,972,023 A | 10/1999 | Tanner et al. |
| 6,506,196 B1 | 1/2003 | Laufer |
| 6,544,271 B1 | 4/2003 | Adams et al. |
| 6,835,199 B2 * | 12/2004 | McGuckin, Jr. | A61B 17/07207 227/175.1 |
| 8,424,741 B2 * | 4/2013 | McGuckin, Jr. | A61B 17/07207 227/176.1 |

* cited by examiner

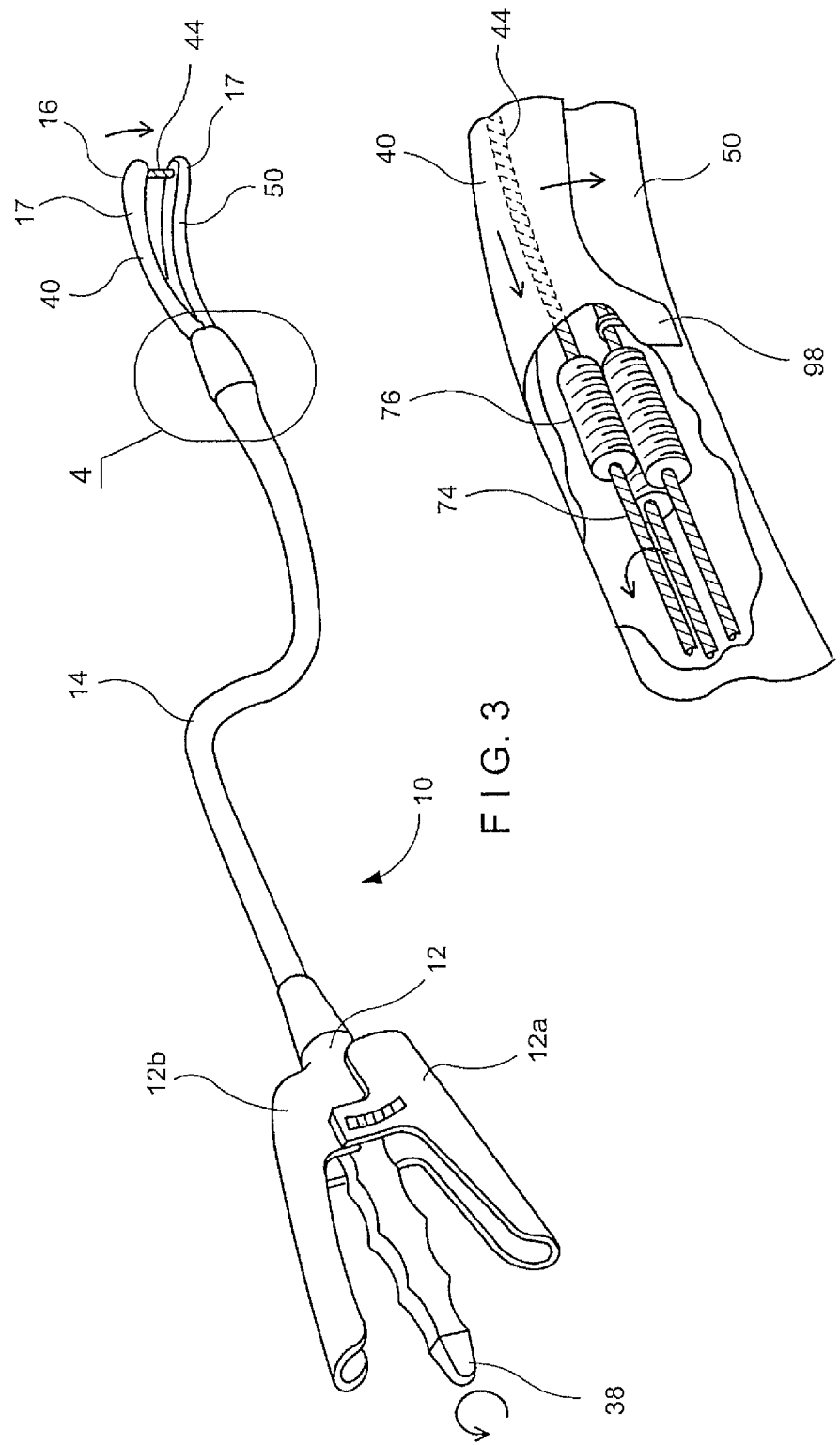

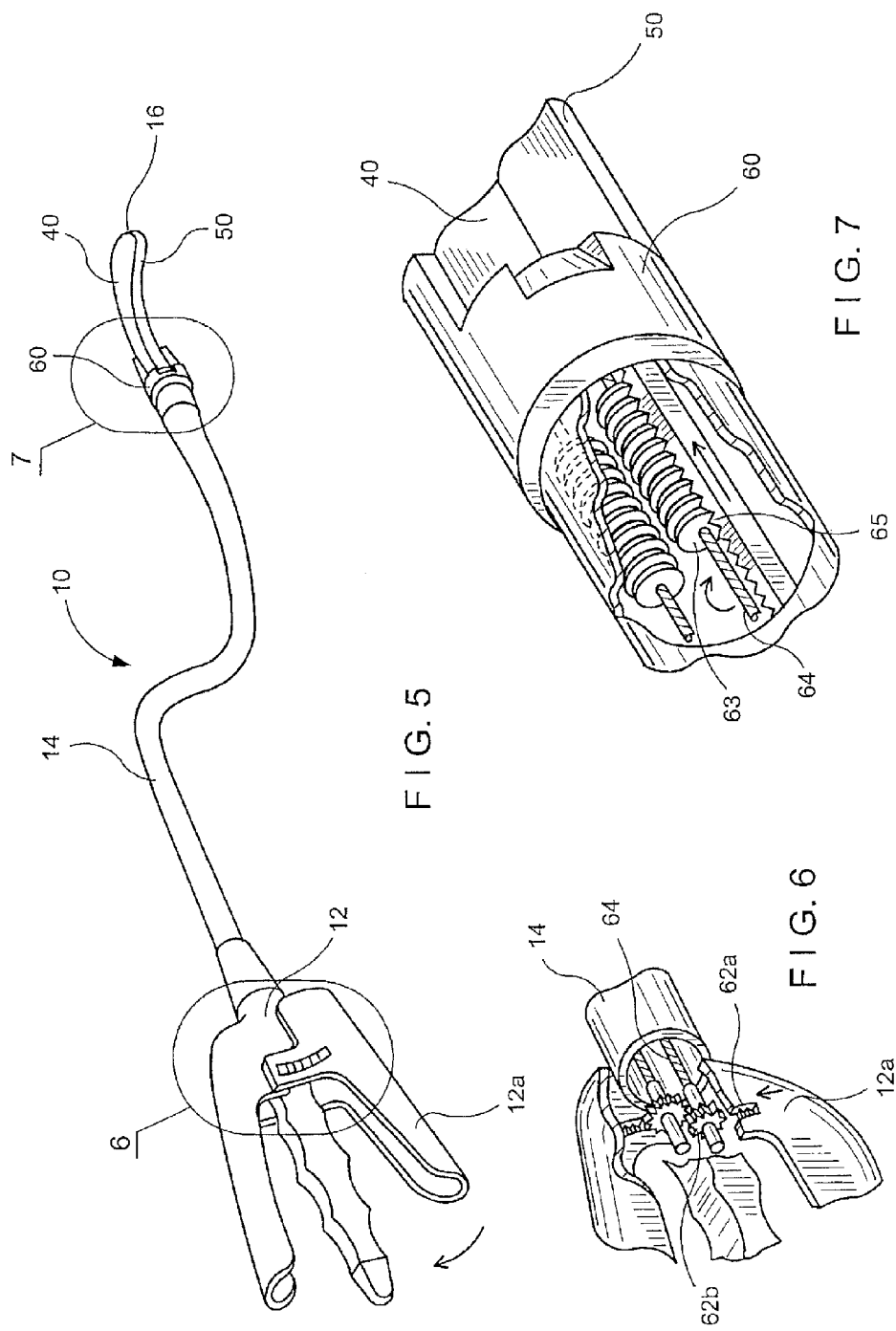

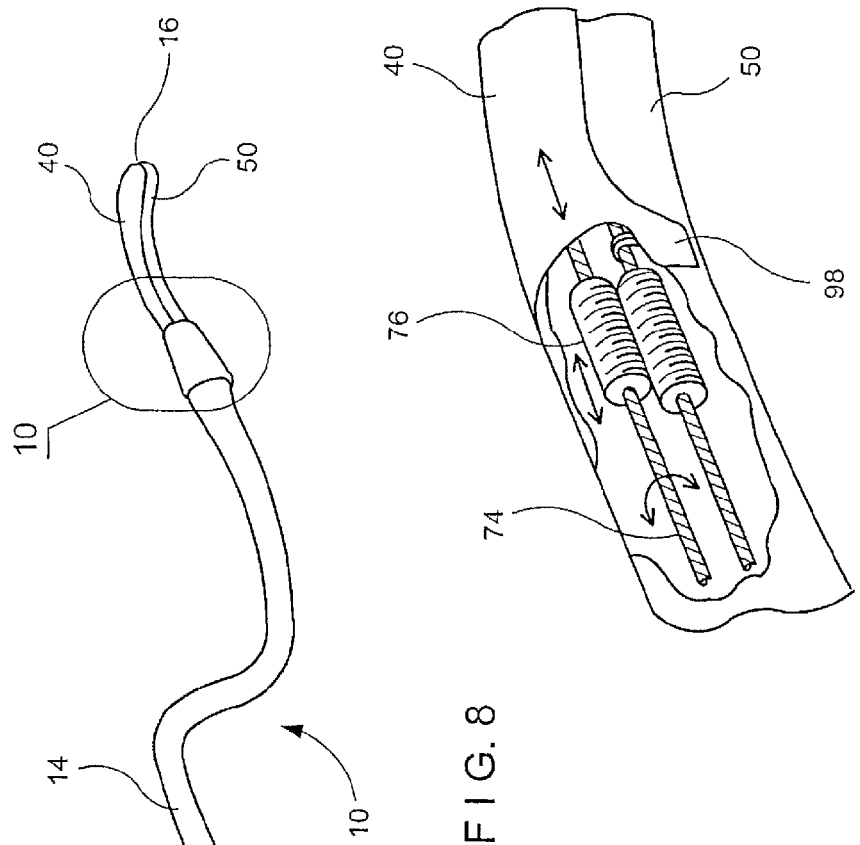
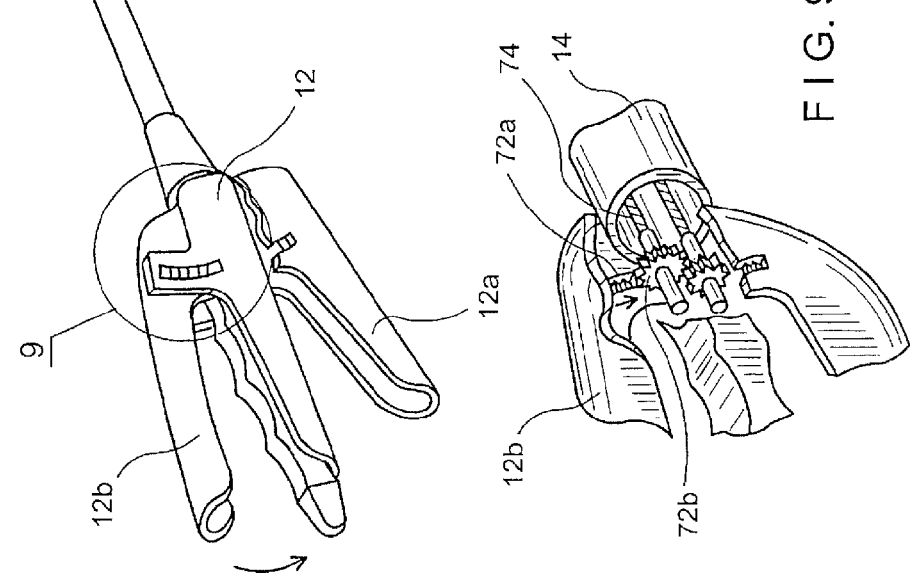
FIG. 8
FIG. 9
FIG. 10

APPARATUS AND METHOD FOR RESECTIONING GASTRO-ESOPHAGEAL TISSUE

CROSS-REFERENCE TO RELATED APPLICATIONS

This application claims prority to and is a continuation of U.S. patent. application Ser. No. 13/856,819, filed Apr. 4, 2013, which is a continuation of U.S. patent application Ser. No. 11/741,126, filed Jun. 20, 2006, which is a continuation of U.S. patent application Ser. No. 10/855,908, filed May 27, 2004, which is a continuation of U.S. patent application Ser. No. 10/062,760, filed Jan. 31, 2002, which claims priority to U.S. Provisional Application No. 60/265,469, filed Jan. 31, 2001, all entitled "Apparatus and Method for Resectioning Gastro-Esophageal Tissue," the entire contents of each of which are incorporated by reference.

FIELD OF THE INVENTION

The present invention relates to endoscopic devices for performing localized resections of gastro-esophageal lesions.

BACKGROUND OF THE INVENTION

Endoscopic surgical stapling apparatus are known in the art and are utilized to provide a variety of surgical procedures. For example, U.S. Pat. No. 5,040,715 to Green, et al. discloses an endoscopic stapling device configured to be inserted through a small entrance wound in the abdominal cavity to place rows of staples in body tissue. This device has a limited range of motion in that the stapling assembly at the distal end of the instrument can only be rotated about the central axis of the instrument.

An endoscopic stapling apparatus purporting to have a greater range of motion is disclosed in U.S. Pat. No. 5,326,013 to Green et al. This device has an articulating stapling assembly mounted for pivotal movement about an axis extending transverse to the central axis of the instrument. An endoscopic stapling device designed to be inserted through a small incision in a body wall and purporting to have an increased range of motion is described in U.S. Pat. No. 5,389,098 to Tsuruta et al. A stapling assembly of this device curves away from a central axis of the instrument to a 90.degree. angle so that it can more easily reach tissue spaced from the central axis. This device incises tissue clamped within the stapling assembly and places staggered lines of staples on both sides of the incision.

SUMMARY OF THE INVENTION

The present invention is directed to a system for stapling tissue comprising a flexible endoscope and an operative head including a pair of opposed, curved tissue clamping jaws sized to pass through an esophagus, the jaws being moveable with respect to one another between an open tissue receiving configuration and a closed tissue clamping configuration, a first one of the curved jaws including a stapling mechanism and a second one of the jaws including a staple forming anvil surface, the stapling mechanism including staple slots through which staples are fired arranged in a row extending from a proximal end of the first jaw to a distal end thereof in combination with a control handle which, when the operative head is in an operative position within one of a patient's stomach and esophagus, remains outside the patient, the control handle including a first actuator for moving the jaws relative to one another and a second actuator for operating the stapling mechanism.

BRIEF DESCRIPTION OF THE DRAWINGS

FIG. 3 shows a perspective view of the system of FIG. 1 with jaws of the stapling apparatus open;

FIG. 4 shows a partially cross-sectional view of a proximal end of the stapling apparatus of FIG. 3 showing control cables for operating the jaws configured as when the jaws are open;

FIG. 5 shows a perspective view of the system of FIG. 1 with jaws of the stapling apparatus closed with a lower actuator lever on a control handle being actuated;

FIG. 6 shows a partially cross-sectional view of the control handle of the system of FIG. 5 showing a coupling between control cables for operating the jaws and the lower actuator lever on the control handle;

FIG. 7 shows a partially cross-sectional view of a proximal end of the stapling apparatus of FIG. 5 showing control cables for operating a stapling pusher of the stapling apparatus configured as when the lower actuator lever is actuated;

FIG. 8 shows a perspective view of the system of FIG. 1 with jaws of the stapling apparatus closed with an upper actuator lever on the control handle being actuated;

FIG. 9 shows a partially cross-sectional view of a portion of the control handle of the system of FIG. 8 showing a coupling between control cables for operating the jaws and the upper actuator lever on the control handle;

FIG. 10 shows a partially cross-sectional view of a proximal end of the stapling apparatus of FIG. 5 showing control cables for operating a stapling pusher of the stapling apparatus configured as when the upper actuator lever is actuated;

DETAILED DESCRIPTION

Figure 1:
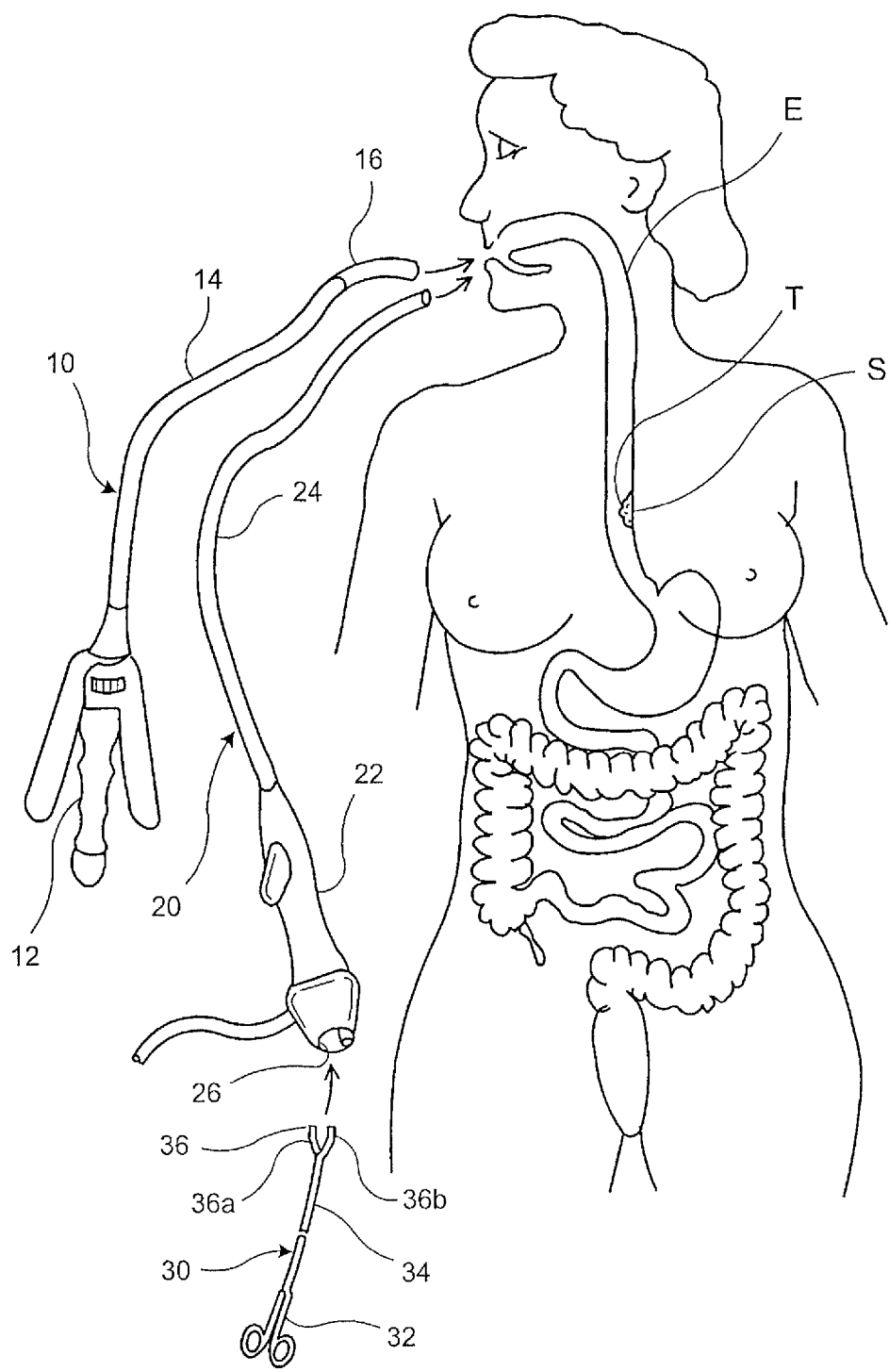
FIG. 1 shows a perspective view of a system according to an illustrative embodiment of the present invention along with a partially cross-sectional view of a patient showing a target portion of tissue to be resected.

A detailed description of illustrative embodiments of the present invention is provided in conjunction with the attached drawings. In the descriptions of the various embodiments and the corresponding drawings, like reference numerals refer to like elements.

A method and apparatus for resectioning anastomized lumenal tissue is disclosed in U.S. Pat. No. 5,868,760 to McGuckin et al., the disclosure of which is hereby incorporated by reference in its entirety. The disclosed apparatus includes a flexible tubular body and a distal operating capsule that may be inserted through either a naturally occurring body orifice or a surgical incision and guided to an operative site endoscopically or using radiologic imaging guidance. In use the target tissue is stapled, cut and captured within the operating capsule for removal from the body. The healthy tissue is thereby anastomized by surgical staples.

FIG. 1 shows a system for resecting esophageal tissue according to an illustrative embodiment of the present invention. A surgical stapling apparatus, designated generally by the reference numeral 10, is utilized in conjunction with an endoscope 20 for providing remote vision of an operative area and to assist in guiding the stapling apparatus 10 to the operative area. An endoscopic grasping device 30 extends through a lumen in the endoscope 20 for use at the surgical site as would be understood by those of skill in the art. Those skilled in the art will further understand that, while the illustrative embodiments are described in conjunction with visual observation of the operative site via the endoscope 20, these procedures may also be visualized through the use of Magnetic Resonance Imaging (MRI). In this case, components of the system and the instruments utilized therewith, such as the grasping device 30, would be constructed from non-ferrous material such as titanium, as would be understood by those of skill in the art.

As shown in FIG. 1, the stapling apparatus 10 includes a proximal handle portion 12, an elongated flexible body portion 14 extending from the handle portion 12 and a generally C-shaped stapling assembly 16 operatively associated with a distal end of the flexible body portion 14. The flexible body portion 14 and the stapling assembly 16 are preferably dimensioned and configured to traverse the natural curvature of the esophagus. As shown in FIGS. 2b and 2c and described in detail below, the stapling assembly 16 includes a pair of opposable jaws 17 defined by a staple carrying portion 40 and a staple forming portion 50. Those skilled in the art will understand that, although the jaws 17 are described herein as rotating relative to one another between the open and closed positions, that these jaws 17 may be coupled by a mechanism which allows them to move linearly with respect to one another or in any other manner so long as they move between a first position in which the jaws 17 are separated from one another to receive tissue and a second position in which the jaws 17 are clamped together to hold tissue tightly therebetween for stapling.

Furthermore, those skilled in the art will understand that the system may operate with any of a variety of commercially available medical endoscopes which may include, for example, a proximal handle portion 22, an elongated flexible body portion 24 through which one or more interior lumena extend for accommodating, for example, a fiber optic bundle or other image transmission structure, a working channel for the grasping device 30, etc. Those skilled in the art will understand that the fiber optic bundle (or other image transmitting structure) allows a user to remotely visually monitor a field of view at the distal end of the endoscope (e.g., an operative site S within the esophagus E). As would be further understood by those of skill in the art, the tissue grasping device 30 may include a handle portion 32, an elongated flexible body portion 34 and a pair of opposable jaws 36a and 36b.

Figure 2A:
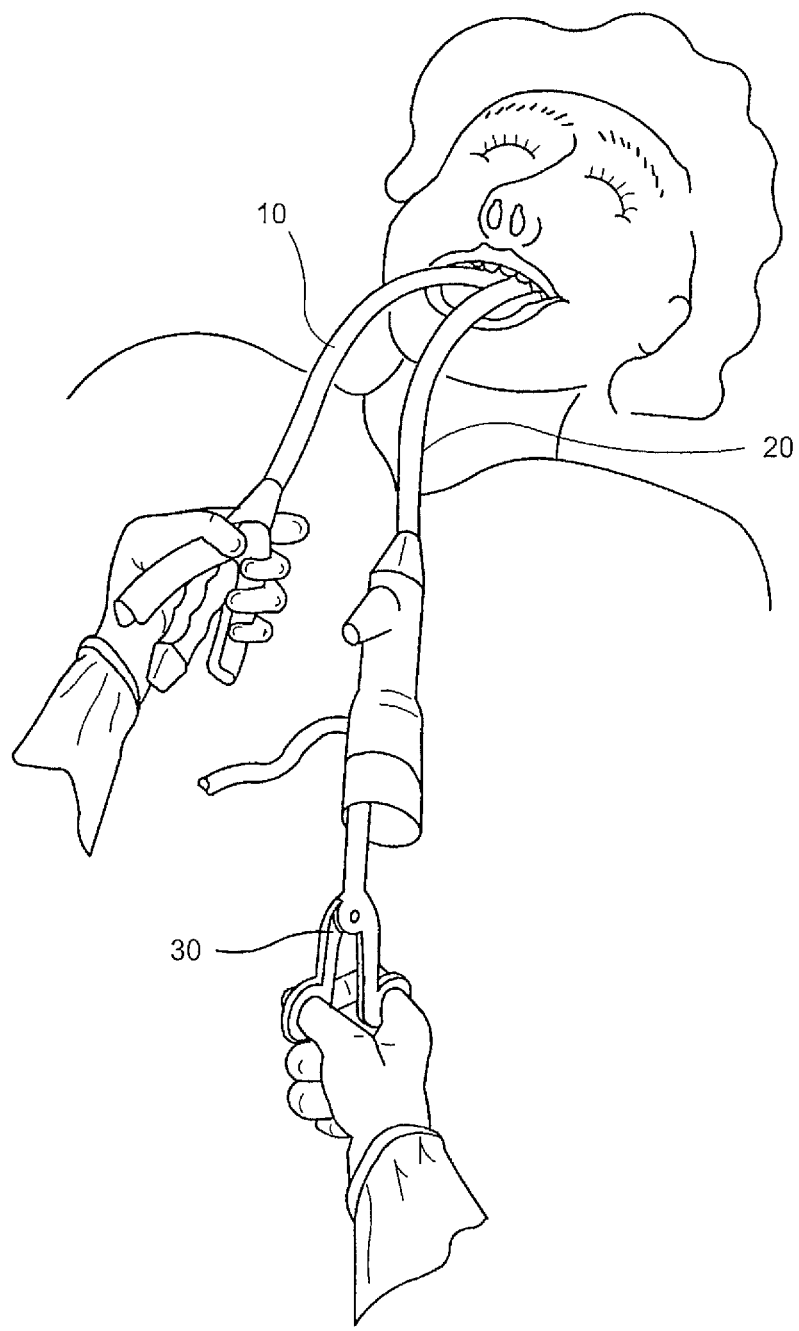
FIG. 2a shows the system of FIG. 1 inserted into the patient's body via the mouth.
Figure 2B:
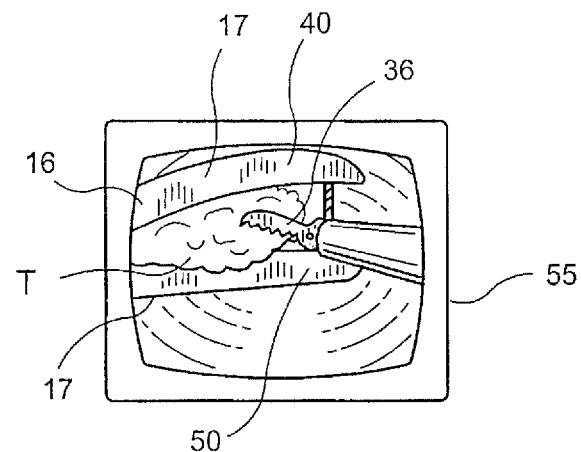
FIG. 2b shows a display of the image of a stapling apparatus of the system of FIG. 1 provided to a user.
Figure 2C:
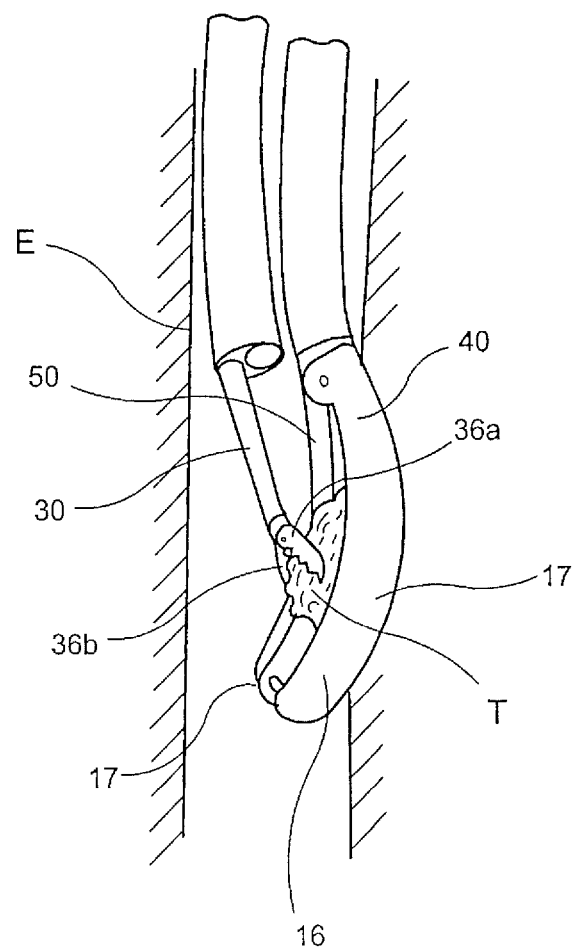
FIG. 2c shows a cross-sectional view of the patient's esophagus with the stapling apparatus of FIG. 3 in position adjacent to the target portion of tissue.

In use as shown in FIGS. 2a-2c, the surgical stapling apparatus 10 and the flexible endoscope 20 are introduced into a patient's mouth and advanced into the esophagus to the operative site S under visual guidance from the endoscope 20. Once at the site S, the operator maneuvers the stapling assembly 16 into a desired position relative to the tissue to be resected. Those skilled in the art will understand that the stapling assembly 16 may be coupled to the handle portion 22 by a cable steering system (not shown) substantially as included in commercially available endoscopes to allow the remote maneuvering and positioning of the stapling assembly 16. The jaws 17 of the stapling assembly 16 are then opened to a tissue receiving position as shown in FIG. 3 and the grasping device 30 is advanced from the distal end of the endoscope 20. The jaws 36a and 36b are rotated away from one another by manipulation of the grasper handle portion 32 and the tissue T to be resected is grasped by closing the jaws 36a, 36b. The grasping device 30 is then withdrawn into the working channel of the endoscope 20 to pull the tissue T into position between the jaws 17 of the stapling assembly 16 and the jaws 17 are closed to clamp the tissue T in place between the staple carrying portion 40 and the staple forming portion 50. Those skilled in the art will understand that the tissue T is preferably drawn between the jaws 17 so that a margin of healthy tissue is positioned between the staple carrying portion 40 and the staple forming portion 50 to ensure that all of the diseased or damaged tissue T is removed. Those skilled in the art will understand that this may be visually confirmed through the use of the vision system of the endoscope as shown in FIG. 2b.

Figure 12:
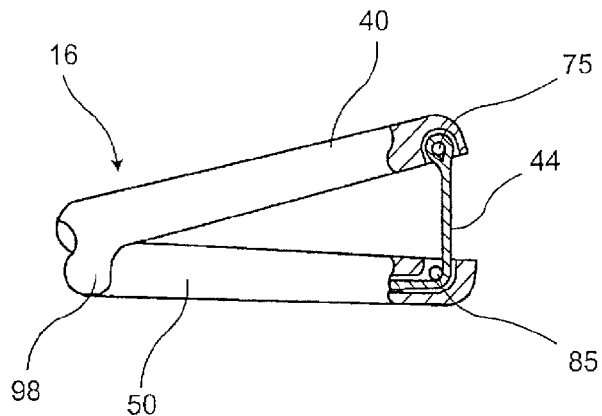
FIG. 12 shows a partially cross-sectional view of the stapling assembly of the system of FIG. 1 illustrating a mechanism for grossly approximating the jaws of the stapling assembly.
Figure 16:
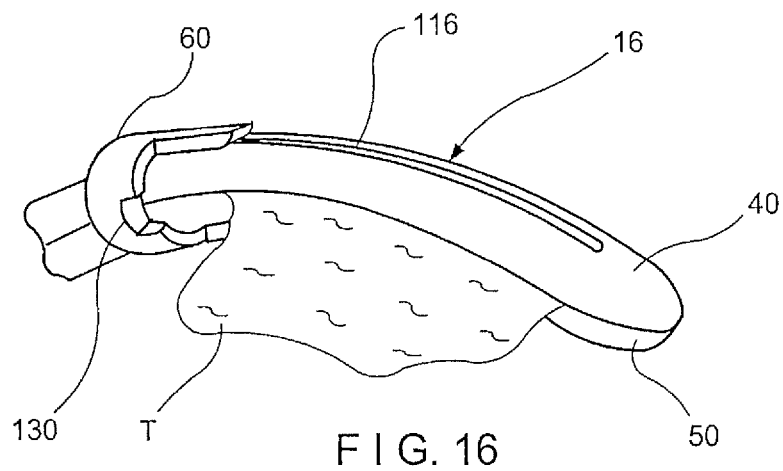
FIG. 16 shows a perspective view of the stapling assembly with a C-shaped clamp member thereof in an initial position.
Figure 17:
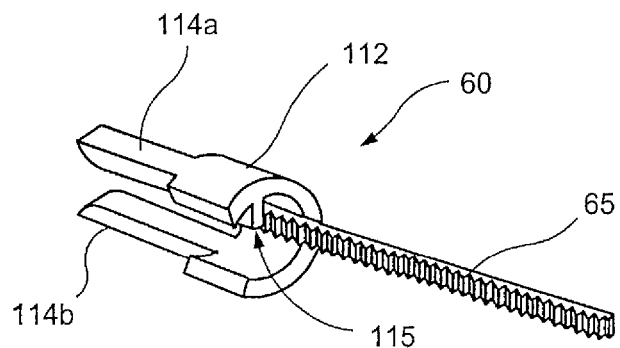
FIG. 17 shows a perspective view of the C-shaped clamp member of FIG. 16 rotated 180.degree. removed from the jaws.
Figure 18:
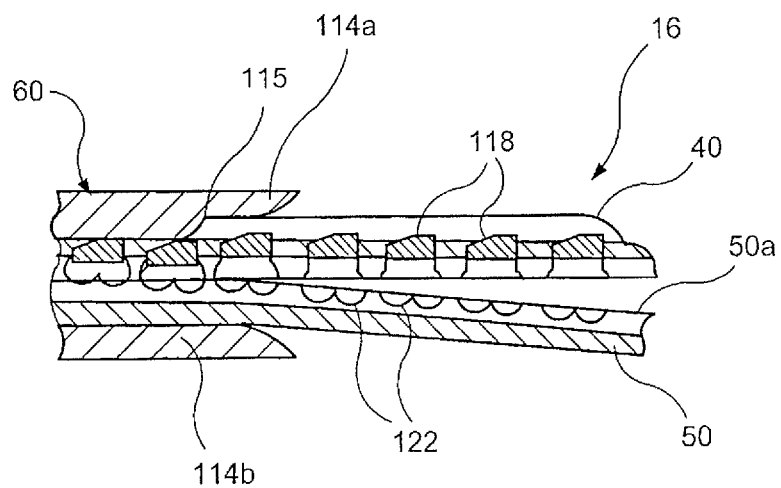
FIG. 18 shows a cross-sectional view of the stapling assembly with the C-shaped clamp member in a partially advanced position.

As shown in FIG. 2c, once the tissue T has been properly positioned between the jaws 17, the jaws 17 are grossly approximated and are then finely approximated using a translating clamping member 60, illustrated in detail in FIGS. 16-18. As shown in FIGS. 3, 4 and 12, an illustrative embodiment of the system according to the present invention includes an actuation cable 44 to facilitate gross approximation of the jaws 17 via actuation of an actuator knob 38. The actuation cable 44 may be secured to the one of the jaws 17 including, for example, the staple carrying portion 40 and is operatively coupled to the other jaw 17 including the staple forming portion 50 by a member 85 which may, for example, be a spindle, capstan or other member around which the cable 44 passes to change direction to generate the clamping force to draw the jaws 17 together. Furthermore, an overhanging flange 98 at a proximal end of the staple carrying portion 40 acts as a tissue shield preventing the target tissue T from entering into the joint between the jaws 17.

As shown in FIGS. 3-7, to actuate the clamping member 60 to finely approximate the jaws 17, the lower clamping handle 12a is actuated in the direction of the arrow in FIG. 5 to cause the integral gear rack 62a to turn pinion gear 62b which rotates elongated drive cable 64. As shown in FIG. 7, the drive cable 64 is coupled to a drive screw 63 so that rotation of the drive cable 64 rotates the drive screw 63 moving the clamping member 60 distally as shown in FIG. 18. This finely approximates the jaws 17 of the stapling assembly 16 whereby a tissue contacting surface of the staple carrying portion 40 and a tissue contacting surface of the staple forming portion 50 are brought into cooperative alignment, tightly clamping the tissue therebetween. Those skilled in the art will understand that alternative sources of power (e.g., electrical, hydraulic, pneumatic, etc.) may be applied to drive the jaws 17 and to drive all other mechanisms of the stapling assembly 16.

As shown in FIG. 8, once the jaws 17 have been brought into cooperative alignment with one another, the stapling assembly 16 may be actuated to fire staples through the, clamped tissue while simultaneously cutting away the tissue T from the stapled and anastamized tissue. The user actuates the stapling assembly 16 to drive staples through the margin of healthy tissue in one or more arcuate bands located radially outward of a line of tissue cutting. Alternatively, those skilled in the art will understand that the stapling operation may be separated from the tissue cutting operation so that no tissue is cut until the entire stapling operation has been successfully concluded.

Specifically, as shown in FIGS. 8-10, the operator drives an I-beam member 70 through the stapling assembly 16 by operating the clamping handle 12b in the direction of the arrow in FIG. 8, causing gear rack 72a to rotate pinion gear 72b which rotates a staple driving drive cable 74 as shown in FIG. 9. The drive cable extends through the flexible body portion 14 to a linear drive screw 76 which drives a flexible pusher 80 coupled to the I-beam member 70 as shown in FIG. 10.

Figure 11:
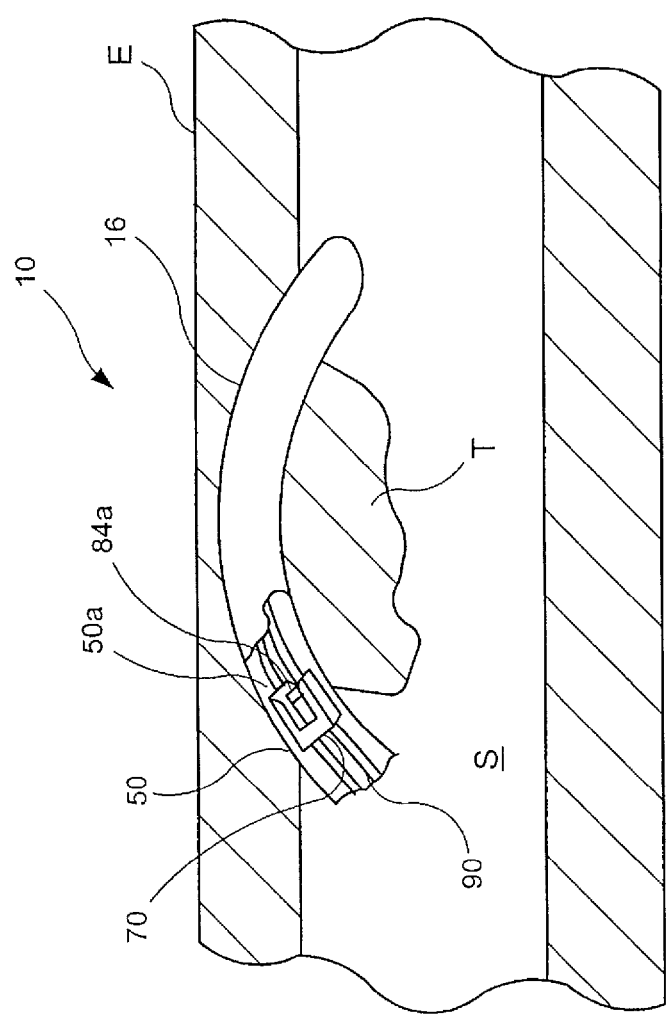
FIG. 11 shows a partially cross-sectional view of a stapling assembly of the system of FIG. 1 grasping esophageal tissue.

As shown in FIGS. 11, 13, 14 and 15, the I-beam member 70 includes upper and lower beam portions 82a, 82b, respectively, connected by a central web portion 84. A leading edge 84a of the central web portion 84 may preferably define a cutting blade for incising tissue as the I-beam member 70 is moved distally as described below. As shown in FIG. 11, an arcuate channel 90 within which the central web portion 84 travels, is defined in the opposing jaws 17 radially inward of the arcuate lines of staple carrying slots (not shown). Those skilled in the art will understand that the staple slots may be arranged in any number of rows, for example, from one to five such rows may be included and the slots of these rows may be staggered so that to ensure that the opening created by the resection is completely sealed.

Figure 13:
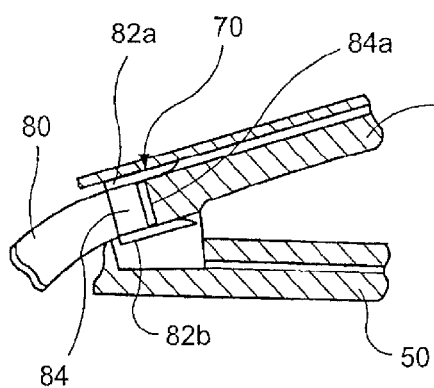
FIG. 13 shows a partially cross-sectional view of the stapling assembly illustrating a mechanism for finely approximating the jaws in an initial position.
Figure 14:
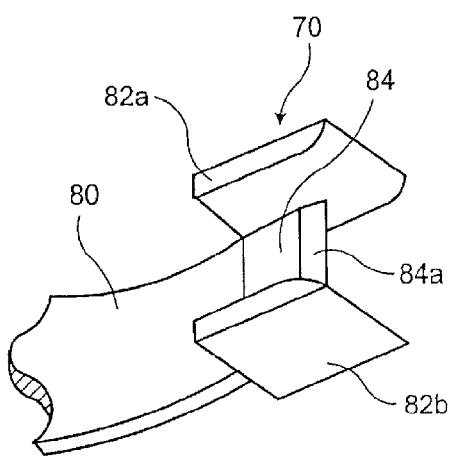
FIG. 14 shows a perspective view of an I-beam member of the fine approximation mechanism of FIG. 13.
Figure 15:
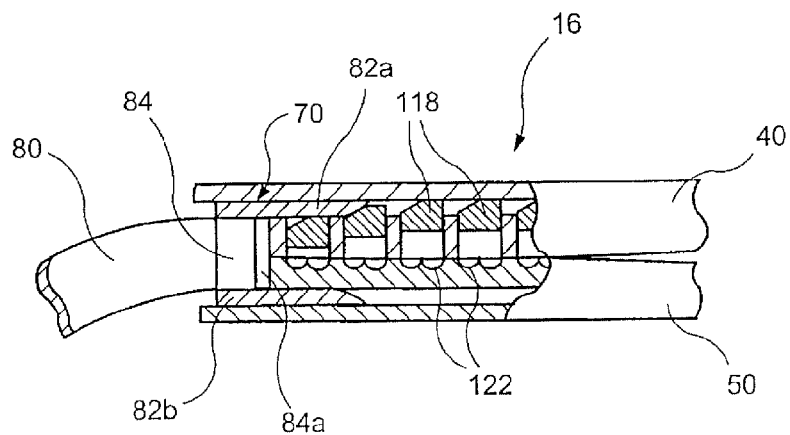
FIG. 15 shows a partially cross-sectional view of the stapling assembly with the fine approximation mechanism in a partially advanced position.

As described above, actuation of the lower handle 12a causes the C-shaped clamp member 60 to move along an arc the length of the curved stapling assembly 16 to finely approximate the jaws 17 toward one another. As shown in FIGS. 13, 14 and 15, the clamp member 60 includes a body portion 112 from which depend upper and lower clamping beams 114a and 114b, respectively, for urging the jaws 17 toward one another.

In addition, as shown in FIGS. 16 and 17, in one embodiment of the invention, the body 112 includes a radially depending driving stem 115 having a sloped leading edge configured to extend through an arcuate slot 116 formed in the staple carrying portion 40 for sequentially contacting each of a plurality of staple pushers 118. The staple pushers 118 are positioned so that, when contacted by the driving stem 115, each staple pusher 118 is driven through a corresponding one of the staple slots to drive a staple housed therein from the slot out of the staple carrying portion 40, through both thicknesses of the folded portion of tissue clamped between the jaws 17 and against the staple forming surface 50a of the staple forming portion 50 to couple the two thicknesses of tissue to one another. In this embodiment, the clamping member 60 further includes an integral cutting blade 130 for forming an arcuate incision substantially concentric with and radially within an inner one of the arcs of staple slots. Furthermore, the cutting blade 130 is preferably positioned so that it trails the leading edge 115 so that tissue is stapled before it is cut.

As shown in FIG. 15, according to a further embodiment of the invention, actuation of the upper actuation handle 12b causes the I-beam member 70 to move through the stapling assembly 16 to sequentially fire arcuate rows of staples while simultaneously cutting tissue away from the esophagus radially within the rows of staples. When the I-beam member 70 is driven by the pusher 80, the sloped leading edge of the upper beam portion 82a contacts sequentially each of a plurality of staple pushers 118 to drive them through their respective staple slots to drive the staples housed therein from each slot out of the staple carrying portion 40, through both thicknesses of the folded portion of tissue clamped between the jaws 17 and into the staple forming pockets 122 formed in the staple forming surface 50a of the staple forming portion 50 to couple the two thicknesses of tissue to one another. As the leading edge 84a of the central web portion 84 is proximal to the sloped leading edge, the incision trails the stapling action so that only tissue within the arc that has previously been stapled is severed.

Figure 19:
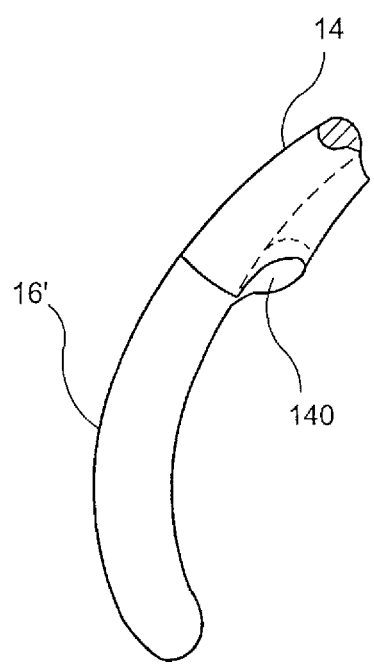
FIG. 19 shows an alternate embodiment of the system according to the present invention with a lateral endoscope receiving lumen.
Figure 20:
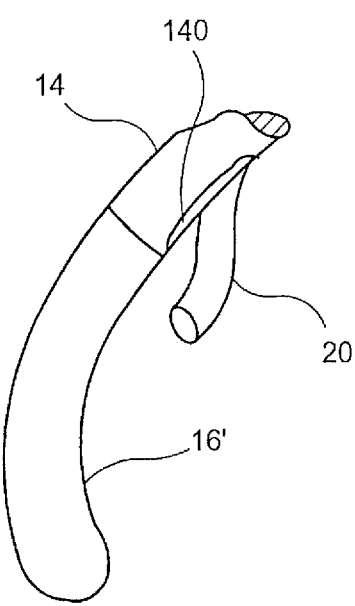
FIG. 20 shows the system of FIG. 19 with an endoscope received therein.

As shown in FIGS. 19 and 20, according to a further embodiment of the invention, a stapling assembly 16' according to the present invention may include an endoscope receiving lumen 140 through which the endoscope 20 may be slidably inserted. This allows an operator to use to steering and vision capability of the endoscope 20 to locate the operative site S. Once the distal end of the endoscope 20 is positioned adjacent to the site S, the stapling assembly 16' may be slid along the endoscope 20 to the operative site S and the steering capability of the distal end of the endoscope 20 may be employed to achieve a desired position and orientation of the stapling assembly 16' relative to the tissue T. Other than the endoscope receiving lumen 140, the construction of the rest of the system of FIGS. 19 and 20 may be substantially in accord with that of any of the previously described embodiments.

Figure 21:
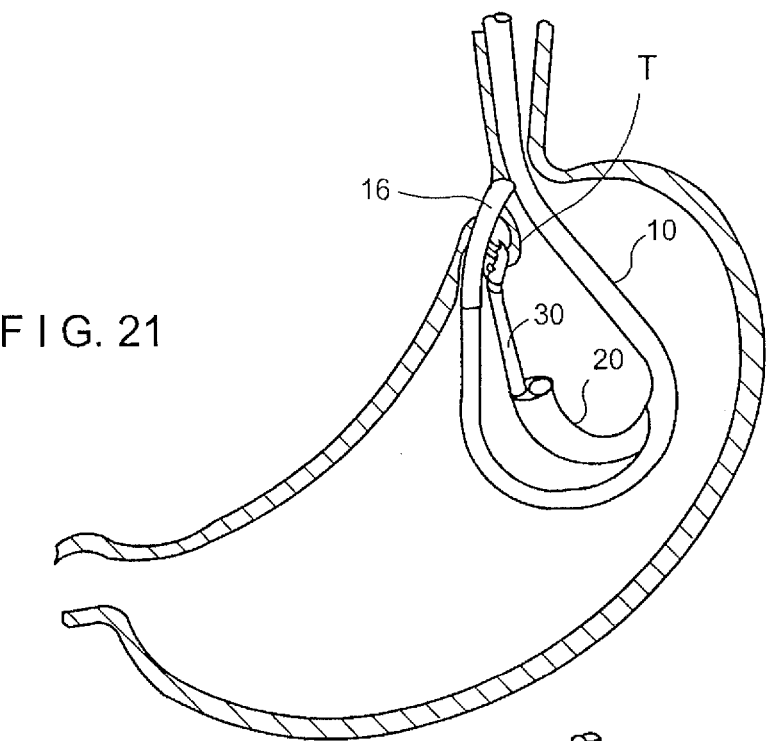
FIG. 21 shows a system in accord with the present invention positioned within the stomach to perform a procedure for the treatment of reflux.
Figure 22:
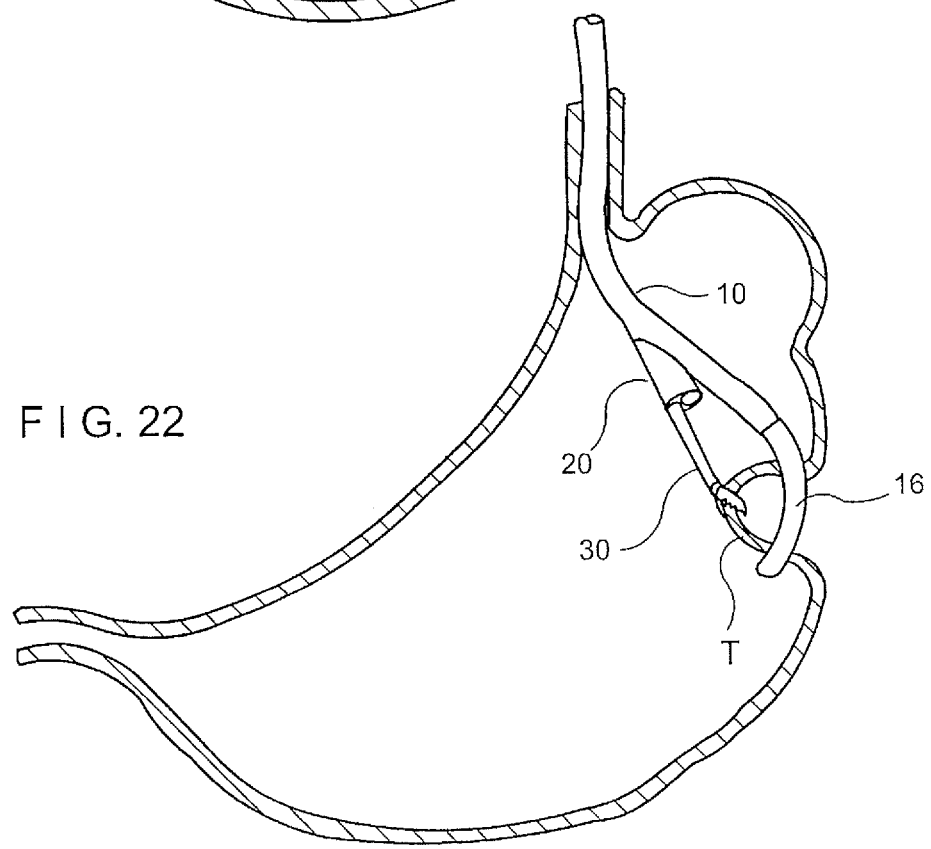
FIG. 22 shows a system in accord with the present invention positioned within the stomach to perform a stomach reduction procedure.

Furthermore, as shown in FIGS. 21 and 22, the system according to the present invention may also be used to perform resections within the stomach. For example, the stapling apparatus 10 may be used to correct gastro-esophageal reflux ("GERD") or to perform a stomach reduction procedure. Specifically, as shown in FIG. 21, a system according to the invention may be inserted through the esophagus into a patient's stomach and the operator may position the jaws 17 under visual control via the endoscope 20 adjacent to a junction between the esophagus and the stomach. The operator then uses the steering capability of the endoscope 20, received within the endoscope lumen 140 to direct the jaws 17 toward a portion of stomach tissue to be fastened to the esophagus. Specifically, the operator grasps a portion of the stomach using the grasping device 30 and urges the tissue T toward the esophagus to create a fold of tissue with an outside surface of the stomach tissue adjacent to or in contact with an outer surface of the esophagus. This fold is then clamped by the jaws 17 and stapled together to reduce the diameter of the opening from the esophagus to the stomach. The tissue radially within the stapled tissue is then resected.

Similarly as shown in FIG. 22, to perform a stomach reduction, an operator inserts a system according to the present invention into the stomach via the esophagus as described above in regard to FIG. 21 and locates a portion of tissue to be folded over on itself to reduce the size of the stomach. This tissue T is grasped by the grasping device 30 and drawn between the jaws 17 which clamp the tissue T together folded onto itself and staples the fold together. Those skilled in the art will understand that, for a stomach reduction procedure, the folded tissue radially within the staples may, if desired, be left in place without resection so that the operation may be reversed at a later date. Thus, for such a stomach reduction procedure where the folded, stapled tissue will be left in place within the stomach, the stapling apparatus 10 need not include a tissue cutting mechanism. Rather, the stapling apparatus 10 need only include structure for approximating the jaws 17 and for driving staples through the gripped fold of tissue. In this case, the C-shaped clamp member 60 would be constructed without the cutting blade 130.

The above described embodiments are for purposes of illustration only and the various modifications of these embodiments which will be apparent are considered to be within the scope of the teachings of this invention which is to be limited only by the claims appended hereto.

What is claimed is:

1. An apparatus, comprising:
   a head having:
   a first jaw and a second jaw, at least one of the first jaw and the second jaw being movable with respect to the other of the first jaw and the second jaw from a first configuration in which the first jaw and the second jaw are spaced apart at a first distance and a second configuration in which the first jaw and the second jaw are spaced apart at a second distance,
   a stapling assembly of the first jaw having slots through which staples are configured to be passed in a row extending from a proximal end of the first jaw to a distal end of the first jaw,
   an anvil surface of the second jaw configured to form a staple,
   a first adjustment assembly configured for gross movement of the first jaw and second jaw,
   a second adjustment assembly configured for fine adjustment of the first jaw and the second jaw; and
   a handle coupled to the head and having one or more actuators configured to move at least one of the first jaw and the second jaw from the first configuration to the second configuration, and to actuate the stapling assembly.

2. The apparatus of claim 1, wherein at least one of the first jaw and the second jaw is curved.

3. The apparatus of claim 1, wherein the second adjustment assembly is one of a clamp coupled around the first jaw and the second jaw, and an I-beam including a web that extends through at least one of the first jaw and the second jaw.

4. An apparatus for stapling tissue, comprising:
   a first jaw and a second jaw, at least one of the first jaw and the second jaw being movable with respect to the other of the first jaw and the second jaw from a first configuration in which the first jaw and the second jaw are separated from each other at a first distance to receive tissue and a second configuration in which the first jaw and the second jaw are clamped together at a second distance to hold tissue therebetween for stapling,
   a staple carrying portion of the first jaw defining slots through which staples are configured to pass;
   an anvil surface defined on the second jaw opposing the first jaw;
   at least one of a gear and a cable operatively coupled to at least one of the first jaw and the second jaw and configured to move at least one of the first jaw and the second jaw from the first configuration to the second configuration such that the first jaw and the second jaw are in alignment; and
   a staple pusher configured to cause a staple to move from a first position at least partially within the staple carrying portion to a second position entirely outside the staple carrying portion, the second distance and the alignment being maintained by a beam configured to engage the first and second jaws from within the first and second jaws while tissue is stapled from a proximal location to a distal location.

5. The apparatus of claim 4, wherein the beam is configured to engage the first and second jaws one of entirely or substantially from therewithin to maintain the second distance and the alignment.

6. The apparatus of claim 5, wherein the beam comprises an upper portion and a lower portion and a web coupled between the upper portion and the lower portion, at least one of the lower portion or the upper portion configured to cause the staple pusher to move a staple as the beam moves from a proximal location to a distal location, the upper portion and the lower portion configured to cooperatively engage the first jaw and the second jaw to align the slots with a staple forming portion on the anvil surface.

7. The apparatus of claim 6, further comprising a cutting blade on the web.

8. The apparatus of claim 5, wherein the beam is configured as a cutting blade.

9. The apparatus of claim 4, wherein the first jaw and the second jaw are pivotably coupled at a pivot point, a portion of the first jaw defining a flange that extends past a surface of the second jaw when the first jaw and second jaw are in the first configuration and the second configuration.

10. The apparatus of claim 4, further comprising one or more actuators including at least one of an actuator handle, a lever, a trigger, a knob or a cable.

11. The apparatus of claim 4, wherein at least a portion of the apparatus is powered.

12. The apparatus of claim 4, wherein at least a portion of the first jaw and the second jaw is curved.

13. An apparatus, comprising:
   a head portion having a first jaw and a second jaw configured to move between a first configuration for receiving tissue and a second configuration for stapling tissue, the first jaw defining a cavity configured to receive a plurality of staples and a plurality of slots configured to pass staples therethrough;

the second jaw having a staple-forming surface; and a beam whose opposite end portions are connected by a central web portion and are configured to clamp and align the first and second jaws from therewithin when in the second configuration as the beam moves distally along a channel defined in a tissue contacting surface of each of the first and second jaws; and a control handle configured to actuate receiving, clamping and stapling of tissue, and a shaft coupling the control handle to the head portion.

14. The apparatus of claim 13, wherein:

the beam is configured to enable at least one of firing staples and cutting tissue.

15. The apparatus of claim 13, wherein the slots through which staples are passed are arranged in a first row extending from a proximal end of the first jaw to a distal end thereof such that two or more staples are fired in a row orthogonal to a direction of movement of the beam one of simultaneously or serially.

16. The apparatus of claim 15, wherein additional slots are arranged in a second row substantially parallel to the first row of slots.

17. The apparatus of claim 13, wherein the head portion is one of fixedly coupled or movably coupled to the shaft.

18. The apparatus of claim 13, wherein tissue is cut between the first row and the second row upon firing of one or more staples through the slots.

19. The apparatus of claim 13, wherein one of the opposite end portions of the beam is configured to enable firing of the plurality of staples.

20. The apparatus of claim 13, wherein the beam includes a cutting blade and is configured to clamp and align the first and second jaws one of entirely or substantially from therewithin.

21. The apparatus of claim 13, wherein one end portion of the beam is configured to cause one or more staple pushers to be pushed for firing the plurality of staples as the beam travels towards a distal end of the head portion.

22. The apparatus of claim 13, wherein the control handle includes at least one of an actuation handle, a lever, a trigger, a knob and a cable.

23. The apparatus of claim 13, wherein at least a portion of the apparatus is powered.

24. The apparatus of claim 23, wherein the apparatus is powered electrically, hydraulically or pneumatically.

25. The apparatus of claim 13, wherein at least a portion of the shaft is flexible.

26. The apparatus of claim 13, wherein at least a portion of the first jaw and the second jaw is curved.

27. An apparatus for stapling tissue, comprising:

a stapling head including first and second jaws, at least one of the first and second jaws being movable to approximate with respect to the other of the first and second jaws, the first jaw including a staple carrying portion and defining slots configured to pass staples therethrough and the second jaw including a staple forming portion; and a beam having upper and lower portions connected by a central web portion, the upper and lower portions being configured to engage the first and second jaws from therewithin, respectively, and the central web portion being configured to travel along a channel defined in each tissue contacting surface of the first and second jaws to clamp tissue therebetween for stapling.

28. The apparatus of claim 27, further comprising:

a control handle configured to actuate driving of staples through the slots and to approximate the first and second jaws; and a shaft coupling the control handle to the stapling head.

29. The apparatus of claim 27, wherein the beam is further configured as a cutting blade and is configured to engage the first and second jaws one of entirely or substantially from therewithin.

30. The apparatus of claim 27, further comprising an endoscope receiving lumen.

* * * * *

(12) INTER PARTES REVIEW CERTIFICATE (2710th)
United States Patent (10) Number: US 9,439,650 K1
Hinchliffe et al. (45) Certificate Issued: May 10, 2022

(54) APPARATUS AND METHOD FOR RESECTIONING GASTRO-ESOPHAGEAL TISSUE

(71) Applicants: Peter W. J. Hinchliffe; James F. McGuckin, Jr.

(72) Inventors: Peter W. J. Hinchliffe; James F. McGuckin, Jr.

(73) Assignee: REX MEDICAL, L.P.

Trial Number:

IPR2020-00152 filed Nov. 19, 2019

Inter Partes Review Certificate for:

Patent No.: 9,439,650
Issued: Sep. 13, 2016
Appl. No.: 15/018,000
Filed: Feb. 8, 2016

The results of IPR2020-00152 are reflected in this inter partes review certificate under 35 U.S.C. 318(b).

INTER PARTES REVIEW CERTIFICATE
U.S. Patent 9,439,650 K1
Trial No. IPR2020-00152
Certificate Issued May 10, 2022

AS A RESULT OF THE INTER PARTES REVIEW PROCEEDING, IT HAS BEEN DETERMINED THAT:

Claims 6-8, 19 and 21 are found patentable.

Claims 4, 5, 9-18, 20 and 22-24 are cancelled.

\* \* \* \* \*